United States Patent [19]

Rosenstatter et al.

[11] 4,325,696
[45] Apr. 20, 1982

[54] DENTAL HANDPIECE ARRANGEMENT

[75] Inventors: Otto Rosenstatter, Seeham, Austria; Reinhard Straihammer, Einhausen, Fed. Rep. of Germany

[73] Assignee: Siemens Aktiengesellschaft, Berlin & Munich, Fed. Rep. of Germany

[21] Appl. No.: 202,138

[22] Filed: Oct. 30, 1980

[30] Foreign Application Priority Data

Nov. 29, 1979 [EP] European Pat. Off. ............ 79104766

[51] Int. Cl.³ .............................................. A61C 1/12
[52] U.S. Cl. ...................................... 433/133; 433/126
[58] Field of Search ......................... 433/133, 114, 126

[56] References Cited

U.S. PATENT DOCUMENTS 3,436,980  4/1969  Loge et al. ........................... 433/105
4,255,143  3/1981  Schuss et al. ....................... 433/126

Primary Examiner—Robert Peshock
Attorney, Agent, or Firm—Hill, Van Santen, Steadman, Chiara & Simpson

[57] ABSTRACT

A dental handpiece arrangement which has a drive transmission for transmitting the rotation from a motor to a socket receiving the tool in the head of the handpiece comprising a first drive shaft having a pair of coaxially arranged drive gears of different numbers of teeth, a second drive shaft having a gear engaging one of the pair of coaxial drive gears characterized by the second drive shaft being composed of a first drive shaft portion and a second drive portion which are interconnected by meshing gears providing a change in the gear ratio. Preferably, the two drive shaft portions of the second drive shaft are mounted in a housing with a gear at each end and the housing is adapted for being supported in the handpiece arrangement in two different positions so that in a first position, a gear at one end is engaging one of the pair of coaxial gears of the first drive shaft and in the second position the gear at the opposite end is engaging the other of the pair. Thus, by changing the position of the housing, a continuous stepping-up of the gear ratio can be obtained or by reversing the position of the housing a continuous stepping-down of the gear ratio can be obtained.

7 Claims, 6 Drawing Figures

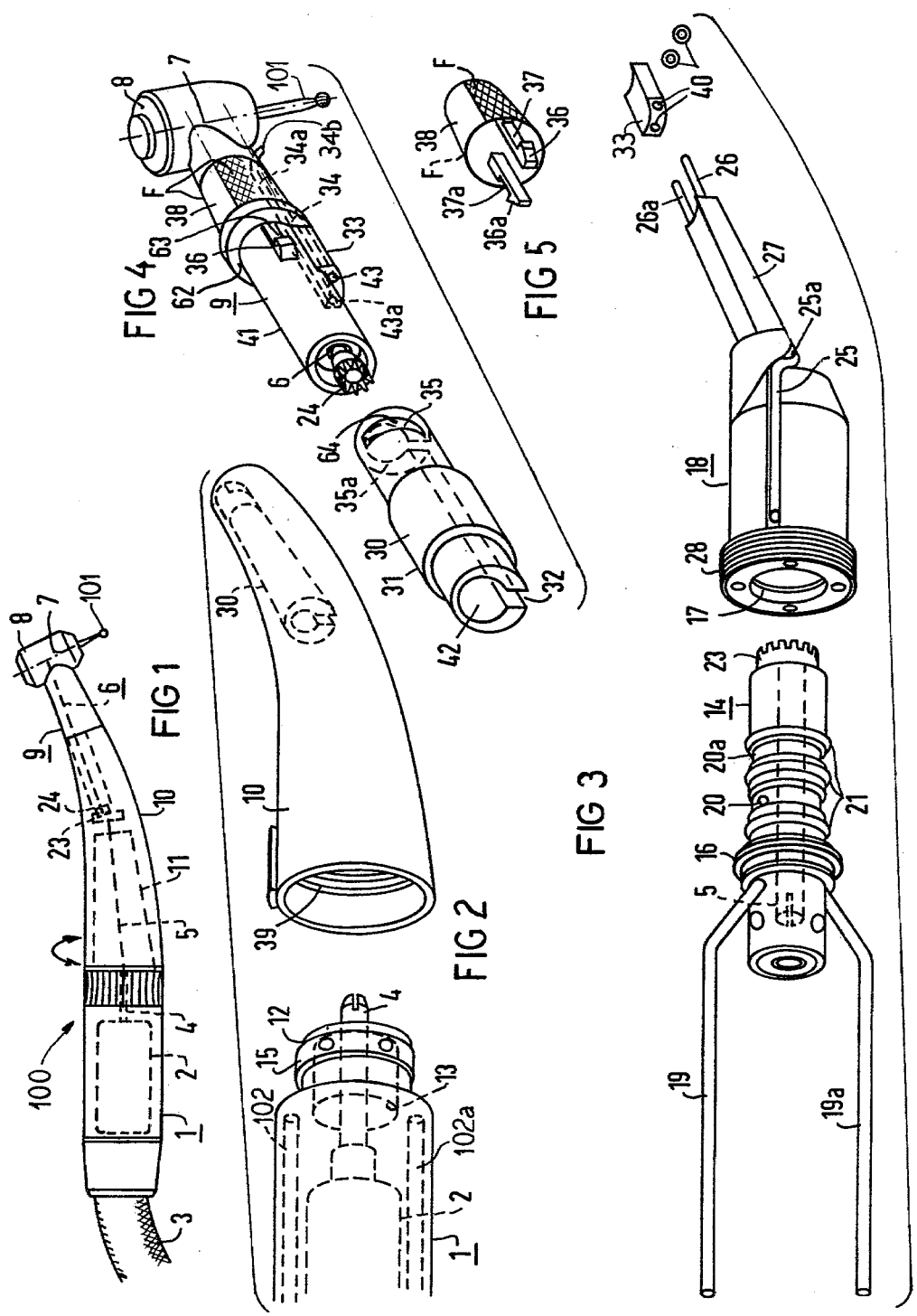

DENTAL HANDPIECE ARRANGEMENT

BACKGROUND OF THE INVENTION

The invention is directed to a dental handpiece arrangement which has a drive transmission including a first and second drive shaft section for transmitting rotary motion from a drive motor to an acceptance sleeve or chuck which receives and rotatably supports a dental tool in the head housing of the handpiece arrangement. In order to obtain a different drive relationship, the first drive shaft has a pair of coaxially arranged gears of different number of teeth so that a different ratio is obtained between the first and second shaft depending on which of the two gears of the first shaft is engaged.

A dental handpiece, which has a drive shaft that is connected to the motor and terminates in a pair of coaxially aligned gears of different number of teeth and has a second drive shaft having a gear engaging one of the pairs of gears, is known and an example is disclosed in U.S. Pat. No. 3,229,369. As disclosed in this patent, the axis of the drive train is divided transversally once along the longitudinal axis of the handpiece so that the two drive shaft sections with gear teeth lying in between are formed. The gear arrangement consists of two coaxial drive gears having mutually different numbers of teeth which are arranged at the end of one drive shaft section essentially in one plane and an individual drive gear arranged on the end of the other drive shaft. By means of interchanging or adjusting the front or head handpiece part relative to the back or rear part, a step-up or step-down of the drive speed can be achieved so that a change in speed of the drive axle can only be undertaken in one transmission direction by means of an interchange or adjustment. For example, from a direct transmission with a transmission ratio 1:1 to a stepped-up with a stepped ratio of 1:3 or from a direct transmission to a stepped-down with a stepped-down ratio of 3:1. In the case of the step-down, the changeable gears is situated in a removable head part together with two coaxial drive gear wheels. In the case of stepped-up, these gear parts are situated in the handpiece part on the drive side. For a stepped-up and a stepped-down of the speed, different drive motors or respectively drive side handpiece parts with appropriately designed drive shaft sections must be provided. Since a Dentist works with both a stepped-down as well as a stepped-up drive speed, he must have a plurality of drive motors or respectively drive side handpiece parts in accordance with the known handpiece arrangements.

Another disadvange of the known handpiece arrangement or design is that the gear wheels required for the gear stepping generally increases the outer diameter of the handpiece parts particularly in the area of the bend given to the angle pieces. In addition, no rotation of the handpiece with respect to the drive part is possible because of the possibility of changing the position of the head part and thus the gear ratio.

In addition, it has proven expedient for the angled handpiece to have a counter bend of approximately 20° with respect to the longitudinal axis of the handpiece. This counter bend is too abrupt and in conjunction with the enlargement of this area as mentioned above, adversely affects the manipulation of the handpiece.

SUMMARY OF THE INVENTION

The object of the present invention is to create a handpiece arrangement which is improved and simplified with respect to achieving a goal of achieving reductions in the size of the handpiece and obtaining both a step-down as well as a step-up in the drive ratio, and if needed a direct transmission of the drive speed to the tool with a single drive part. In addition, the present invention strives to be able to reduce the outside diameter particularly in the area of the change in the gear ratio and to create a softer transition in the area of the counter bend of the angled handpiece.

To accomplish these tasks, the present invention is directed to an improvement in a dental handpiece arrangement having a drive transmission with at least two drive shafts for transmitting rotational motion of a drive motor to an acceptance sleeve which rotatably supports the dental tool in the head of the dental handpiece arrangement. The drive transmission includes a first drive shaft having a pair of coaxially arranged drive gears mounted at one end with each gear having a different number of teeth, a second drive shaft having a gear at one end for meshing engagement with one of said pair of coaxial drive gears. The improvement comprises the second drive shaft being composed of two drive shaft sections interconnected in a driving relation by drive gears having different number of teeth so that a change in the speed of rotation occurs between the two drive shaft sections. Preferably, the two drive shaft sections of the second drive shaft are supported in a housing and the housing is constructed to be alternately inserted into the dental handpiece with the first end positioned to have a gear thereon in engagement with one of the coaxial gears of the first drive shaft and a second position with the other end positioned for a gear to be engaged with the other of said pair of coaxial gears. Thus, in one position, when the gear of the second drive shaft is engaged with the larger of the two coaxial gears and when the drive gear which interconnects the pair of drive shaft sections has a stepping-up in the drive ratio, it is possible to obtain a stepping-up in the drive ratio to occur between the pair of drive shaft sections and between the end of the second shaft and the acceptance sleeve for the dental tool. In the other position, it is possible to have a stepping-down in the drive ratio to occur in each point of gear meshing.

Preferably, the pair of gears interconnecting the drive sections together includes an outside tooth spur gear and an inside tooth spur gear. A particularly useful embodiment of the invention has the dental handpiece arrangement having an angled handpiece part and the housing for the second drive shaft is mounted in the angled portion of the angled handpiece part so that the axis of rotation of the drive shaft sections lie on an axis extending at an angle to the axis of the first drive shaft. In addition, the angled handpiece part preferably has means for releasably connecting the angled handpiece part onto a housing of the first drive shaft and the angled handpiece part includes a shank having means for securing the housing of the second drive shaft and the handpiece without axial twisting thereof.

By means of the proposed invention, one achieves the advantage that it is a significant higher degree of stepped-down and/or stepped-up such as approximately 30% can be achieved. The prior known constructions did not have such a degree of stepping-up or stepping-down in the drive ratio.

BRIEF DESCRIPTION OF THE DRAWINGS

FIG. 1 is a side view of a dental handpiece arrangement in accordance with the present invention;

FIG. 2 is a partial exploded perspective view of the dental handpiece arrangement of FIG. 1;

FIG. 3 is a partial exploded perspective of internal parts of the dental handpiece arrangement of FIG. 1;

FIG. 4 is another partial exploded view of the head portion and internal parts of the handpiece arrangement;

FIG. 5 is a perspective view of a portion of the headpiece arrangement illustrated in FIG. 4.

DESCRIPTION OF THE PREFERRED EMBODIMENTS

Figure 6:
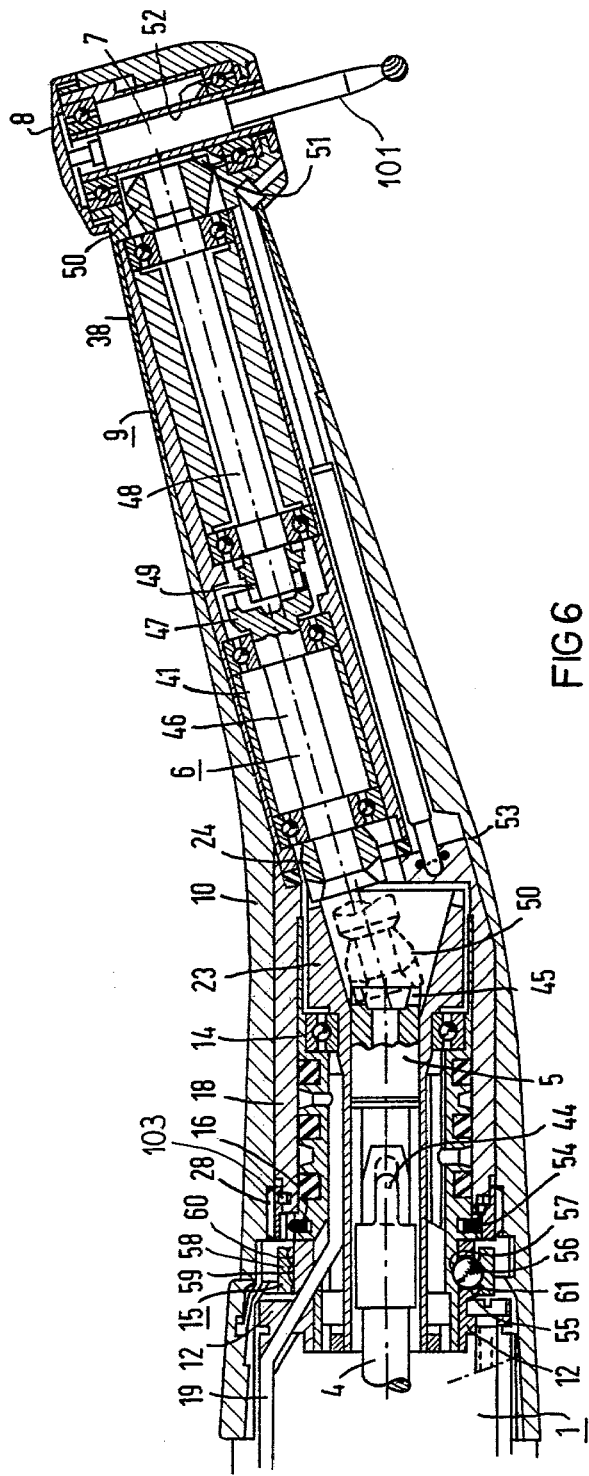
FIG. 6 is a longitudinal cross-section of a portion of the dental handpiece arrangement of FIG. 1.

The principles of the present invention are particularly useful in a dental handpiece arrangement generally indicated at 100 in FIG. 1.

The handpiece arrangement 100 is composed of a drive section or part 1, an angled portion or piece 10 and a head part or portion 9. The drive section or portion 1 contains a drive motor 2 for example an electric motor 2, which receives its drive energy by a supply hose 3 and has a drive shaft 4. In the angled portion 10, a drive train composed of drive shafts 5 and 6 transfer rotational motion or output from the drive shaft 4 to a rotatable tool acceptance shaft or socket 7 that receives and supports a dental tool such as a drill 101 for rotation in a head housing 8 of the headpiece 9. The head housing 8 is part of the head part 9 which accepts the two drive shaft section 6 and 7 as well as their bearings and which is removably seated on a handpiece gripping sleeve 10 which is an angled portion. The sleeve 10 encloses a bearing unit 11 which is formed of two concentric sleeves 14 and 18 (FIG. 3) that have bearing units for the drive shaft section 5 as well as the rotational connection for conveying one or more cooling agents from the drive part or section 1 to the head part or section 9. The handpiece gripping sleeve 10 together with the head part 9 and the bearing unit 11, which will be described in greater detail below, will rotate with respect to the drive part 1 around the longitudinal axis of the handpiece which is the axis of the drive shaft 4.

The drive part 1 (FIG. 2) has a sleeve like or cylindrical shoulder 12 surrounding a socket 13 indicated in broken lines through which the drive shaft 4 extends. The socket 13 receives one end of the sleeve 14 when the handpiece parts are assembled. On an outer surface of the shoulder or sleeve 12, a ball catch 15 is provided for axially securing the sleeve 14 in the socket 13. The sleeve 14, which is best illustrated in FIG. 3, contains a spring washer 16 which engages into a snap ring groove 17 of a sleeve 18 during assembly. The sleeves 14 and 18 form the bearing unit 11. Two cooling agent lines 19 and 19a are secured to the sleeve 14 and the ends of the cooling lines discharged in a known manner via radial bores or ports into annular channels 20 and 20a, which are sealed from one another by means of packing rings such as O-rings 21. In addition the sleeve 14 also accepts and supports the first drive shaft 5 which has one end connected to the drive shaft 4 of the motor 2 and the opposite end supporting a bell-shaped drive gear 23 which will be engaged with the gear 24 (FIG. 4) on the drive shaft section 6. In the assembled state, the ends of the cooling lines sections 19 and 19a will project from the sleeve 14, are engaged in longitudinal grooves and/or bores 102, 102a, of a drive housing of the drive part 1 and can be connected to a supply lines which are conveyed in the hose 3.

In an assembled state, sleeve 18 (FIG. 3) is arranged concentric to the sleeve 14 and contains the coolant line sections 25 and 25a which in turn accept the coolant agent from the annular grooves 20 and 20a in a known manner. The coolant lines 25 and 25a terminate in tubular prongs 26 and 26a which are mounted in a diagonally extending portion or extension 27 of the sleeve 18. The sleeve 18 further contains a threaded ring 28, which is rotatably mounted on the sleeve 18 by a pin arrangement 103 (FIG. 6) and contains the snap ring groove 17 for engagement with the spring washer 16 when the sleeve 18 is assembled on the sleeve 14. The sleeve 18 is axially secured in the handpiece by means of the threaded ring 28 being threaded into threads 39 (FIG. 2) of the sleeve of the grip portion 10.

The grip portion or part 10, as illustrated in FIG. 2, adjacent the head 9 receives a resilient slotted guide bushing 30. As best illustrated in FIG. 4, the bushing 30 has a collar 31 which is snapped into a socket of the grip portion 10. The guide bushing 30 is thus secured in the handpiece portion 10 against axial slippage. As illustrated, the guide bushing 30 is provided with a cylindrical bore 42 and a continuous longitudinal slot 32 which receives the projecting portion 27 of the sleeve 18 and also a longitudinal fitting strip or member 33 of the head part 9. As illustrated, the strip 33 of the head part 9 contains cooling agent line sections 34 and 34a which discharge into a common cooling agent discharged nozzle 34b in the area of the tools supported in the head 8.

The guide bushing 30 serves to prevent twisting of the part 18 relative to the part 9 and also contains two circumferentially spaced catch slots 35 and 35a which are shown as being on both sides of the bushing. The slots 35 and 35a receive radial resilient catch noses 36 and 36a when the head part 9 is axially assembled onto the grip section or portion 10. The two catch noses 36 and 36a are secured on a spring-like tubular sleeve 38 (FIG. 5) by means of bridges 37 and 37a which extend parallel to the axis of the sleeve. The spring sleeve 38 is designed with a very thin wall and is arranged on the head part 9 in such a manner that it forms an outer generated surface. By means of radial pressure against the sleeve 38 for example by using the thumb and index finger, the two catch noses 36 and 36a can be moved radially towards the inside and therefore will be released or disengaged from the slots 35 and 35a.

The bridges 37 need not be absolutely rigidly arranged at the actuation sleeve 38. It is also conceivable within the framework of the invention for the head 9 to be connected to the grip portion 10 by a friction type lock for example by insertion in the guidance groove of the grip portion. Variations of the sample embodiment illustrated are also possible with respect to the number of catch noses provided without leaving the framework of the invention. The disposition of the two catch noses lying diametrically opposite one another, however, is particularly advantageous although it is also conceivable to provide only one catch nose or three or respectively four catch noses for specific purposes. An embodiment in which the resilient sleeve is provided with one or more recesses on a circumference and the bridges together with the catch noses are arranged on the member 30 is also within the framework of the present invention.

For assemblying the handpiece arrangement, the bushing 30 is first clamped into the grip portion 10. The collar 31 is thus engaged in the corresponding socket of a sleeve-like grip portion 10 and prevents axial dislocation of the bushing. Subsequently, the sleeve 18 is inserted into the handpiece portion 10 with the projection 27 engaged in the longitudinal slot 32 of the guide bushing 30. By means of the threaded ring 28, which is rotatably mounted on the sleeve 18, the sleeve 18 is axially fixed within the handpiece portion 10 as the threads of the ring 28 are received in the internal threads 39. The sleeve 14 as already mentioned is connected in a twist proof but axially releasable manner on the drive part 1 by means of the ball catch device 15. The handpiece grip or sleeve portion 10 with the guide bushing 30 supported therein and the sleeve 18 with the cooling agent lines 25 and 25a can now be axially slipped onto the sleeve 14 until the spring washer 16 is received by the groove 17 and the two handpiece parts are then axially fixed or connected together.

The head part 9 in addition to including the spring like sleeve 38 has a tubular shank or neck part 41 with a portion of the fitting strip 33 extending from one side thereof. When the head part 9 is assembled with the grip portion 10. the shank 41 is received in the bore 42 of the bushing 30 and the strip 33 is received in a portion of the slot 32. Thus the head part 9 will be secured against twisting relative to the bushing 30 and to the sleeve 18. Prior to assembly, elastic seal 40 consisting of one or more elements are inserted over the prong-like projections 26 and 26a of the coolant lines 25 and 25a. Thus, during assembly the prongs 26 and 26a will be received in sockets 43 and 43a of the member 33 to complete the connection to the cooling agent line sections 34 and 34a. The amount of insertion of the shank into the bore 42 is limited by a shoulder 62 but not until after the catch noses 36 and 36a have been engaged in the catch slots 35 and 35a so that the head part 9 is first axially fixed with respect to the grip sleeves or portions 10. In the catch position, the seals guarantee a tight connection between the cooling line sections 25 and 34.

In addition, the seals 40 also fulfill another function namely providing sufficient clearance between the two gears 23 and 23 for proper meshing engagement. To this end, the two catch noses 36 and 36a are engaged in the slots 35 and 35a with a slight axial play. The pre-stress force created by the seals 40 will bias the head part 9 away from the grip sleeve 10. Thus, the desired clearance between the handpiece parts in the axial direction is obtained due to the detent of the edge 63 of the catch nose 36 and 36a being engaged tightly against the sides 64 of the slot such as 35 and 35a. Due to this arrangement, the shoulder 62 can be eliminated.

Instead of utilizing the elastic seals 40, a spring wire, a spring band or the like can be exerted at right angles to the cooling fluid line sections 34. These spring members can be provided to act on an end face of the fitting strip or member 33 or a part thereof to urge the head part 9 away from the gripping sleeve 10. This biasing ensures the axially effective pressure and spacing between the two gears 23 and 24 when the handpiece parts are properly connected.

For releasing the head part 9, the spring sleeve 38 is pressed slightly together in a radial direction in the surface areas F which are a knurled outer portion adjacent each of the catch noses 36 and 36a. By means of this pressing together, which is expediently accomplished by the thumb and index finger, the spring sleeve is deformed thereby moving the catch nose from an engagement in the respective slots. The arrangement of the catch connection in the area illustrated allows a safe connection and disconnection of the handpiece parts because the head part need be grasped particularly only at the side surfaces, which are the surface areas which merge tangently into the head housing 8.

The structure and the arrangement of the drive shaft sections is best illustrated in FIG. 6. The first drive shaft 5 is directly coupled to the drive shaft 4 of the motor 2 by a dog coupling 44. On the end opposite the dog coupling, the first drive shaft section contains two coaxially aligned drive gears with different numbers of teeth. This is mainly the drive gear 23, which is a bell gear and is concentrically arranged around crown gear 45 which is smaller in diameter. The second drive shaft 6, which is supported for rotation by bearing in the sleeve or shank 41 of the head part 9 is composed of a first drive shaft sections 46 and a second drive shaft section 48. As illustrated, the first drive shaft section 46 on one end has the gear 24 and on the opposite end has a gear 47 and the second drive shaft section 48 has a gear 49 which is in meshing relationship with the gear 47 and on an opposite end has a gear 50. Each of the drive shaft sections 46 and 48 are supported in the shank 41 by bearings with their axes being parallel to each other. The gear pairing of the larger diameter gear 47, which is an inside tooth spur gear, with the smaller diameter outside spur gear 49 creates a step-up in the drive ratio of 1:1.5 between the shafts 46 and 48. The gear 50 at the end of the drive shaft section 48 faces the head housing and is designed as a conical gear which engages a gear 51 on the drive shaft 7 which supports the acceptance sleeve or chuck 52 that accepts the rotary tool such as 101.

The two drive shaft sections 46 and 48 as seen in FIG. 6 are supported in the head part 9. Thus, in a narrow sense they are also components of the housing of the head part 9 in particular the shank portion 41. In the position illustrated in FIG. 6, rotary motion is first transmitted from the drive shaft 4 of the motor 2 directly to the drive shaft 5. Due to the engagement of the bell-shaped gear 23 of the drive shaft 5 with the crown 24 of the drive shaft 46, the rotary motion is thus transmitted to the first drive shaft section 46 of the second drive shaft 6. In view of the size relationship of the gears 23 and 24, a stepping-up of the motor speed in the ratio of 1:2.1 is obtained. By means of the gear pairing 47 and 49, as already mentioned any additional step-up in the ratio of 1:1.5 is achieved. A further, however, smaller step-up in the ratio of 1:1.3 is achieved in the head housing 8 by means of the relationship of the gear 50 to the gear 51. Thus, in the arrangement illustrated in FIG. 6, in bold lines, a total step-up ratio of 1:4.1 is obtained.

As a result of the subdivision of the second drive shaft 6 into the two sections 46 and 48, it is possible to also obtain a step-down in the drive ratio using the same drive shaft part in a reverse order while retaining the gear pairing 47 and 49. For example, by reversing the position of the housing formed by the shank 41, the gear 50, which was previously engaged with the gear 51, will become engaged with the smaller crown gear 45 of the first drive shaft 5 as illustrated in broken lines. Also, the gear 24 will engage with the gear 51 on the drive shaft 7. Although the gear meshing of the gears 47 and 49 is retained, it is in the reverse order so that a step-down will occur therebetween. Thus, by utilizing a connection having the crown gear 45 of the first drive shaft 5 engaged with the crown gear 50 of the shaft 48, a 1:1 drive ratio is obtained. In this arrangement a step down will occur due to the relationship between the gears 47 and 49.

The two drive shaft sections 46 and 48 can be advantageously designed in such a manner and arranged in the head part 9 so that they can be arranged in one of the other two arrangements completely with their bearings or in the alternative can be built as a unit which can be assembled in either one of the two positions. Thus, a gear pairing can be formed in which the gear tooth relationship between the two drive shafts 46 and 48 is interchanged and the drive gears are reversed and arranged in a reverse sequence. For example, either a gear pairing 23/24; 49/47; and 50/51 or a gear pairing 45/50; 47/49; and 24/51. The number of drive shaft parts to be fabricated can thus be reduced by means of the above described interchangeability.

The sleeve 18 is axially fixed in the grip sleeve 10, which covers the drive shaft sections 5 and also covers the drive shaft section 6 over a large part, by means of the threaded ring 28. To this end, both the grip sleeve 10 as well as the sleeve 18 are provided with a section 53 serving as a positioning guide. The threaded ring 28 contains the groove 17 which is adapted to receive the spring washer 16 and the spring washer 16 is inserted radially resiliently in a groove 54 of the sleeve 14. When the sleeves 10 and 18 are connected to one another by means of the threaded ring 28, and the combination is axially placed on the sleeve 14, the spring washer 16 snaps into the spring washer groove 17 of the threaded ring 28. The gripping sleeve 10 with the head part 9 secured thereto is then axially secured with respect to the drive part 1. By means of overcoming a specific axial tension or force, the grip sleeve 10 with the part secured thereto can then be removed from the sleeve 14. The spacing of the engagement between the gear pairs such as 23 and 24 or respectively 45, 50 can also be adjusted by use of the threaded ring 28.

The sleeve 14 is removably secured in the socket 13 by catch means 15, which is mounted on the sleeve part 12 of the housing for the drive part 1. The catch means 15 contains three balls 56 which are inserted in circumferentially spaced radial bores 55 of the sleeve 12 and the balls 56 are engaged in recesses 57 of the sleeve 14. The balls 56 are pressed radially inwardly into the recesses 57 by means of a retention ring 58. The retention ring 58 contains a first snap ring groove 59 adapted to the ball surface and a second snap ring groove 60 adapted to the surface of the spring washer 16. The snap ring groove 60 serves for the indissoveable support of the retention ring 58 when the sleeve 10 is removed. By means of displacing the retention ring 58 towards the right, i.e. towards the head part 9, the retention ring together with the snap ring 60 can thus be placed over the spring washer 16. In this position, the balls 56 can move radially outward, but, however, only up to a detents 61 which is located at the radial groove or bore 55. This detent is dimensioned in such a manner that the sleeve 14 can be axially removed from the sleeve 12.

In the disclosed sample embodiments, the axis of the two drive shaft sections 46 and 48 lie parallel to one another, however, it can also be advantageous to seat the drive shafts in such a manner that their axes intersect at an angle and the teeth of the gear such as 47 and 49 will be designed similar to the teeth of the gears such as 23 and 24. In such a situation, the entire counterbend angle, i.e. the angle which is formed between the motor axis and the axis of the drive shaft section 48 can be increased.

Although various minor modifications may be suggested by those versed in the art, it should be understood that we wish to embody within the scope of the patent granted hereon, all such modifications as reasonably and properly come within the scope of our contribution to the art.

We claim:

1. An angled handpiece arrangement being detachably connected to a housing of a drive motor and having a drive transmission for transmitting rotational motion of the drive motor to a chuck which rotatably supports a dental tool in a head of the dental handpiece arrangement, said handpiece arrangement comprising a sleeve member having means for forming a detachable connection to the housing of the drive motor, said sleeve member having a first portion for supporting a first drive shaft for rotation, said first drive shaft having a pair of coaxially arranged drive gears mounted on one end with each gear having a different number of teeth, said sleeve member having a second portion extending at an angle to the first portion and receiving a shank of a head of the dental handpiece arrangement, said shank and second portion having means for releasably connecting the shank in the second portion without any twisting therebetween, a second drive shaft being composed of two drive shaft sections interconnected in driving relation by two drive gears having a different number of teeth so that a change in the speed of rotation occurs between the two drive shaft section; and said second drive shaft being disposed in said shank with an end being engaged with one of the coaxial gears of the first shaft so that the axis of rotation for said pair of drive shaft sections lies on an axis extending at an angle to the axis of the first drive shaft.

2. An angled handpiece arrangement according to claim 1, wherein the two drive gears interconnecting the drive shaft sections together includes an outside toothed spur gear and an inside tooth spur gear.

3. A dental handpiece arrangement being detachably connected to a housing of a drive motor and having a drive transmission for transmitting rotational motion of the drive motor to a chuck which rotatably supports a dental handpiece in the head of the handpiece arrangement, said handpiece arrangement comprising a housing member having means for forming a detachable connection to the housing of the drive motor, said housing member having a first portion for supporting a first drive shaft for rotation, said first drive shaft having a pair of coaxially arranged drive gears mounted on one end with each gear having a different number of teeth with one gear being a large gear and the other being a small gear, said housing member having a second portion receiving a housing element containing a second drive shaft being composed of two drive shaft sections interconnected in driving relation by drive gears having a different number of teeth so that a change in the speed of rotation occurs between the two drive shaft sections, said two drive shaft sections having a gear extending from each end of the housing element, said housing element being constructed to be alternately inserted in the housing member of the dental handpiece arrangement in a first position with one end positioned with a gear thereof in engagement with the larger gear of the coaxial gears of the first drive shaft and a second position with the other end positioned for a gear to be engaged with the smaller gear of said pair of coaxial gears so that while in the first position a stepping up occurs between the first drive shaft and the second drive shaft, between the second drive shaft and the chuck for the dental tool and in the second position, a stepping down occurs with each of the parts with meshing gears.

4. A dental handpiece arrangement according to claim 3, wherein the pair of gears interconnecting the drive sections together includes an outside tooth spur gear and an inside tooth spur gear.

5. A dental handpiece arrangement according to claim 4, wherein the dental handpiece arrangement is an angled dental handpiece arrangement, said housing member has an angled portion, said housing element of the second drive shaft being mounted in the angled portion so that the axis of rotation of each of the drive shaft sections lie on an axis extending at an angle to the axis of rotation of the first drive shaft.

6. A dental handpiece arrangement according to claim 3, wherein the dental handpiece arrangement is an angled dental handpiece arrangement, said housing member has an angled portion, said housing element of the second drive shaft being mounted in the angled portion so that the axis of rotation of each of the drive shaft sections lie on an axis extending at an angle to the axis of rotation of the first drive shaft.

7. A dental handpiece arrangement according to claim 6, wherein the angled portion of the housing member has means for receiving a shank of the head of the handpiece, said housing element being received in the shank, said angled portion and shank having means coacting for releasably connecting the shank into the housing member without axial twisting thereof.

* * * * *